(12) United States Patent
Clarke, Jr. et al.

(10) Patent No.: US 11,497,646 B2
(45) Date of Patent: Nov. 15, 2022

(54) SELF INFLATING SEX AID

(71) Applicants: Harry S. Clarke, Jr., Sullivans Island, SC (US); Rebecca DeLegge, Awendaw, SC (US); Lauren Elizabeth Eskew, Ellicott City, MD (US)

(72) Inventors: Harry S. Clarke, Jr., Sullivans Island, SC (US); Rebecca DeLegge, Awendaw, SC (US); Lauren Elizabeth Eskew, Ellicott City, MD (US)

(*) Notice: Subject to any disclaimer, the term of this patent is extended or adjusted under 35 U.S.C. 154(b) by 459 days.

(21) Appl. No.: 16/570,484

(22) Filed: Sep. 13, 2019

(65) Prior Publication Data

US 2020/0085612 A1 Mar. 19, 2020

Related U.S. Application Data

(60) Provisional application No. 62/730,888, filed on Sep. 13, 2018.

(51) Int. Cl.
*A61F 6/04* (2006.01)
*A61F 5/41* (2006.01)

(52) U.S. Cl.
CPC .............. *A61F 6/04* (2013.01); *A61F 5/41* (2013.01); *A61F 2005/411* (2013.01)

(58) Field of Classification Search
CPC ...... A61F 6/04; A61F 6/065; A61F 2006/042; A61F 6/146; A61F 6/06; Y10S 128/918; A61B 10/0058
See application file for complete search history.

(56) References Cited

U.S. PATENT DOCUMENTS

| | | |
|---|---|---|
| 4,281,648 A | 8/1981 | Rogers |
| 4,798,600 A | 1/1989 | Meadows |
| 4,805,604 A | 2/1989 | Spery |
| 4,840,188 A | 6/1989 | Heidenfelder |
| 4,856,534 A | 8/1989 | Sorkin et al. |
| 4,875,358 A | 10/1989 | Marsh et al. |
| 4,966,165 A | 10/1990 | Anderson |
| 4,972,849 A | 11/1990 | Park et al. |
| 5,284,158 A | 2/1994 | Mallette |
| 5,318,043 A | 6/1994 | Burr et al. |
| 5,331,974 A | 7/1994 | Sook |
| 5,351,699 A | 10/1994 | Hammons |
| 5,377,692 A | 1/1995 | Pfeil |

(Continued)

FOREIGN PATENT DOCUMENTS

CN 203408152 1/2014

OTHER PUBLICATIONS

Penelope Eugenia Webb, Chemical Inflation for Assisted Assembly, Submitted Paper for degree of Master of Science, Aug. 28, 2017. https://www.media.mit.edu/projects/auto-inflatables.

*Primary Examiner* — Ophelia A Hawthorne
(74) *Attorney, Agent, or Firm* — B. Craig Killough

(57) ABSTRACT

A sexual aid useful for men that have some degree of erectile dysfunction. The device inflates to provide rigidity for sexual intercourse, or to assist in maintaining an erection. Inflation of the device according to the invention results from the reaction of non-toxic chemicals. The gas inflates a condom and supports the condom in a posture that is sufficiently rigid to facilitate sexual intercourse or inflates a constriction ring and holds blood in the penis that may maintain sufficient erectile function to facilitate sexual intercourse.

19 Claims, 8 Drawing Sheets

(56) References Cited

U.S. PATENT DOCUMENTS

| | | | |
|---|---|---|---|
| 5,429,141 | A | 7/1995 | Korsinsky et al. |
| 5,433,219 | A | 7/1995 | Spery |
| 5,531,230 | A | 7/1996 | Bell |
| 5,598,852 | A | 2/1997 | Spery |
| 5,823,191 | A | 10/1998 | Cho |
| 5,885,205 | A | 3/1999 | Kassman |
| 5,927,278 | A | 7/1999 | Omrani |
| 6,074,671 | A | 6/2000 | Oldham et al. |
| 6,098,626 | A | 8/2000 | Kim |
| 6,651,668 | B1 | 11/2003 | Praml |
| 6,796,311 | B1 | 9/2004 | Zarakowski |
| 6,895,967 | B2 | 5/2005 | Praml |
| 8,074,653 | B2 | 12/2011 | Madigan et al. |
| 9,844,458 | B2 | 12/2017 | Yun |
| 2007/0144529 | A1* | 6/2007 | Bryant ............... A61F 6/04 128/844 |
| 2013/0090524 | A1 | 4/2013 | McNamara |
| 2013/0221181 | A1 | 6/2013 | Hamilton |

* cited by examiner

SELF INFLATING SEX AID

Applicant claims the benefit of U.S. Provisional Application Ser. No. 62/730,888, filed Sep. 13, 2018.

BACKGROUND OF THE INVENTION

Some men have partial erectile dysfunction. There is a need for a device that assists men who are able to obtain a partial erection, but the erection is less than satisfactory for sexual intercourse, or men who have other problems related to sexual dysfunction.

SUMMARY OF THE INVENTION

The present invention is a sexual aid, such as a condom or a constriction ring, used for men that have some degree of erectile dysfunction. The device inflates to provide rigidity for sexual intercourse, or to assist in maintaining an erection. The device is particularly useful for men who are able to obtain a partial erection, but the erection is less than satisfactory for sexual intercourse.

Inflation of the device according to the invention results from the reaction of non-toxic chemicals. These chemicals produce a non-toxic gas, such as carbon dioxide, to inflate the condom. The gas inflates the condom and supports the condom in a posture that is sufficiently rigid to facilitate sexual intercourse. The gas inflates the constriction ring and holds blood in the penis that may maintain sufficient erectile function to facilitate sexual intercourse.

A constriction ring may form the proximal end of the condom. Alternatively, an inflatable constriction ring is disclosed that may be used without the condom, or used with the condom of the invention, or used with other condoms.

BRIEF DRAWING DESCRIPTION

DESCRIPTION OF PREFERRED EMBODIMENTS

Figure 1:
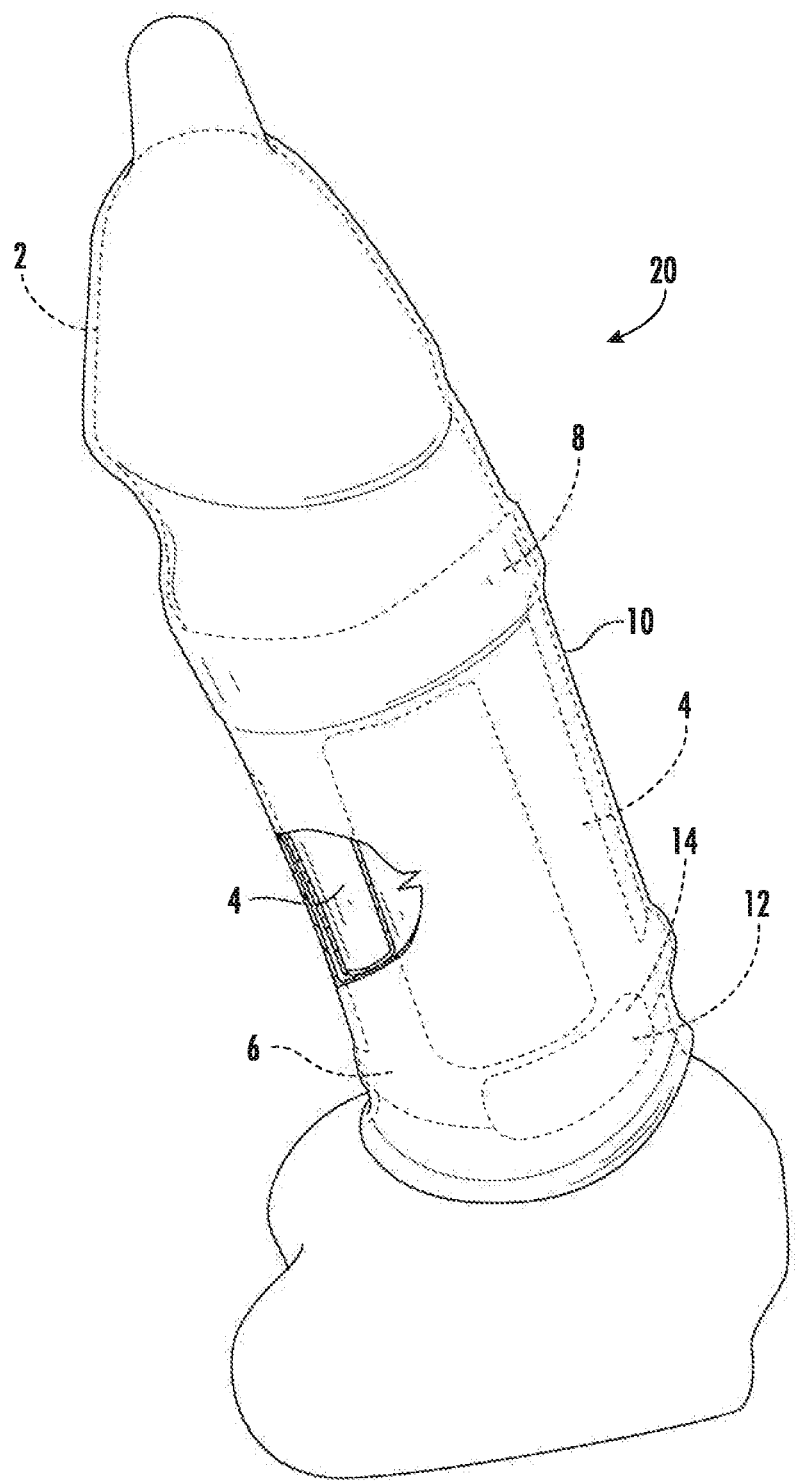
FIG. 1 shows a condom according to an embodiment of the invention. A model simulating a partially erect penis is depicted within the condom.

The condom according to the invention is characterized by a condom 20 having a sheath 10 formed of latex, polyurethane, polyisoprene or other materials from which condoms are commonly formed. The sheath is constructed to cover at least a portion of the penis.

According to the embodiment of the invention shown in FIGS. 1-4, an inflatable frame is provided that is constructed and arranged to support the sheath 10 and elongate the sheath when the frame is inflated. The inflatable frame may be formed by a plurality of inflatable lumens 4, 6, 8. The lumens may be interconnected so that gas flows between them. The lumens are substantially gas impermeable, and are sufficiently gas impermeable so as to maintain the sheath by gas pressure in a posture sufficient to achieve sexual intercourse for a typical period of time for sexual intercourse.

The lumens 4, 6, 8 receive and hold gas produced by a chemical reaction. As the chemical reaction occurs to produce a gas, the lumens forming the frame of the device inflate and expand to form a condom construct that is sufficiently rigid to facilitate sexual intercourse.

According to an embodiment of the invention, at least two (2) materials are positioned in the condom 20. The materials, when introduced to each other, react to form a gas for inflation of the condom. The materials may be present at or near a proximal end, or open end, of the condom. The materials may be separated by a membrane or membranes prior to use. The membrane(s) prevent the reactive materials from interacting and reacting until reaction is initiated by the user.

In one embodiment, a chamber construct 12 at a proximal end of the condom communicates with a first annular lumen 6. The plurality of lumens 4 extend from the first annular lumen to communicate with a second annular lumen 8.

Figure 2:
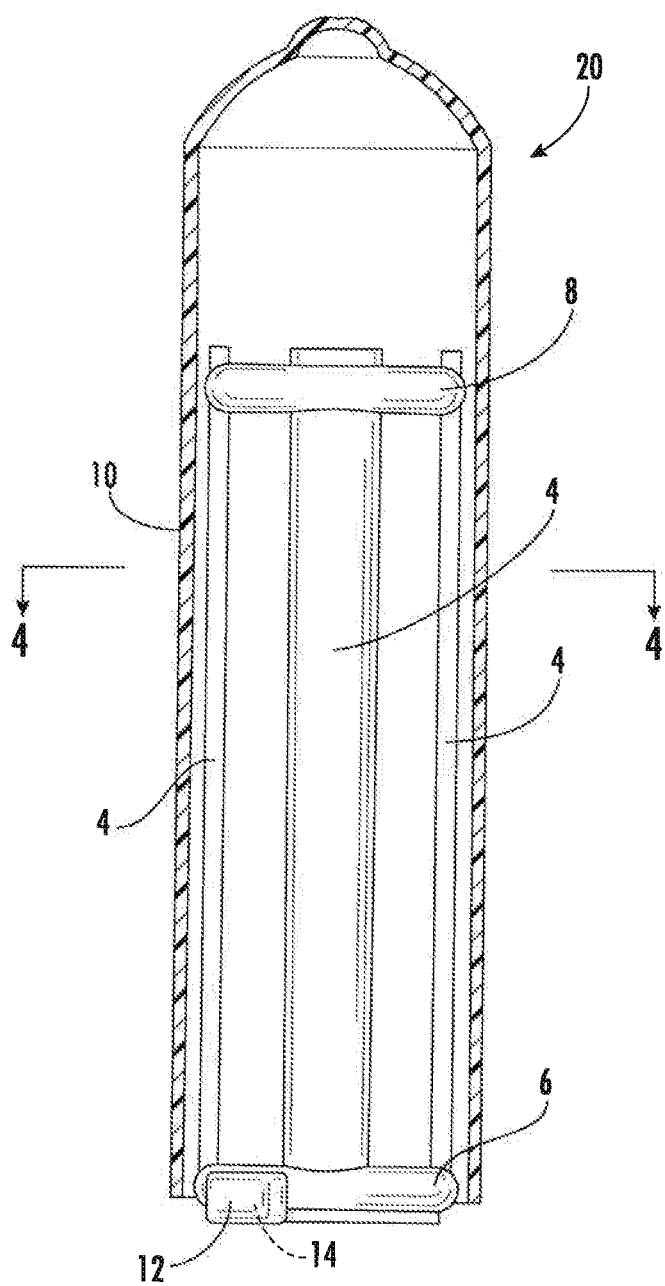
FIG. 2 is side, sectioned view of a condom according to an embodiment of the invention. The sheath is sectioned to reveal an inflatable frame for the condom.
Figure 3:
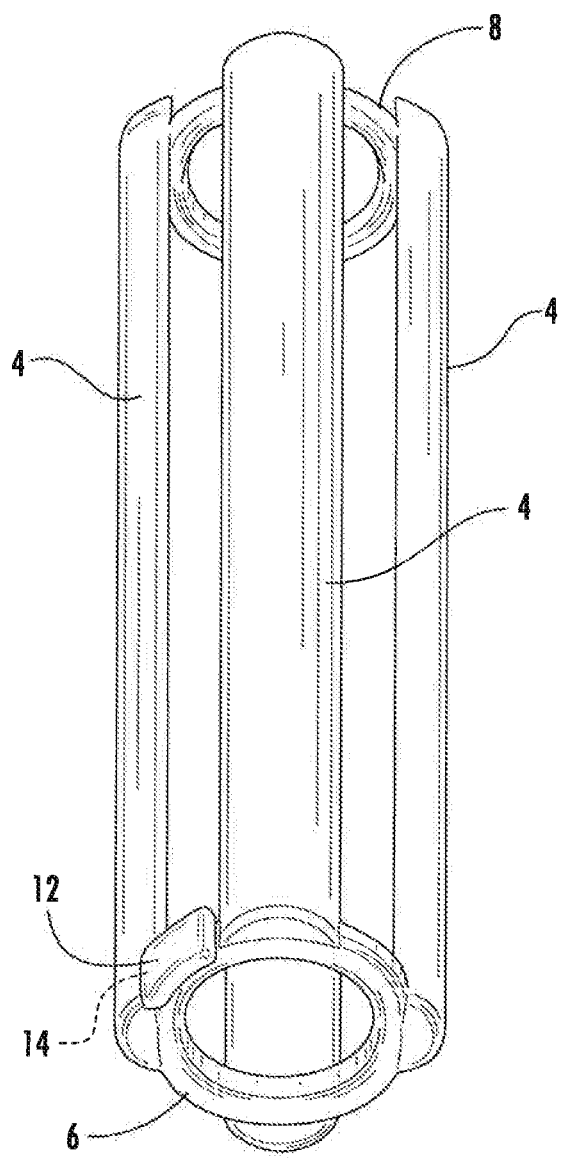
FIG. 3 is a perspective view of an embodiment of an inflatable frame for the condom according to an embodiment of the invention.
Figure 4:
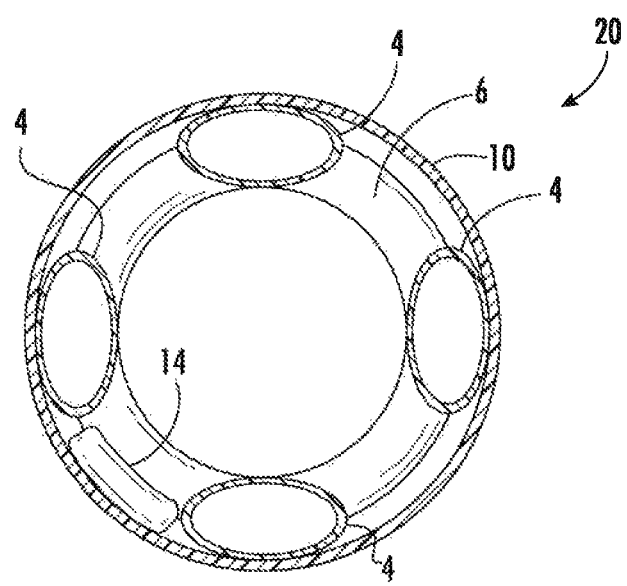
FIG. 4 is a sectioned view of an embodiment of the condom

In the embodiment shown in FIG. 2, a first or proximal annular lumen 6 and a second, or distal, annular lumen 8 are provided. A plurality of elongated lumens 4 extend along the length of the condom 20 from the first annular lumen 6 to the second annular lumen 8, providing communication between the first annular lumen and the second annular lumen. The second annular lumen is positioned at or near an opening of the condom at the proximal end of the condom into which the user's penis is inserted.

The first annular lumen 6, the plurality of lumens 4 and the second annular lumen communicate 8 in a network so that gas is transmitted from the chamber 12 to provide inflation of the frame construct formed by the lumens. Two or more elongated lumens 4 may be provided. As shown in the drawings, four (4) elongated lumens 4 are used to form the frame of the condom construct.

The plurality of elongated lumens 4, the first annular lumen 6 and the second annular lumen 8 are provided with a quantity of gas that will hold the condom in a sufficiently rigid condom construct that will support a partially erect penis. The condom 20, and a penis that is present therein, are held by the gas inflated frame construct in an elongated position that is sufficiently rigid to facilitate sexual intercourse.

The lumens may be formed of a non-compliant material, or semi-compliant material and may be formed of latex, nylon, polyethylene terephthalate (PET), urethane, or polymers that are capable of inflation as described herein.

Gas for inflating the condom is provided by a chemical reaction. A gas is produced from the chemical reaction that is non-toxic and not harmful to the user in the event of breakage. The gas may be carbon dioxide. Similarly, the materials used to produce the gas for inflation of the condom should be non-toxic and not harmful to the user in the event of undesired or unintended breakage of the membrane that separates the materials.

An example of chemicals that produce carbon dioxide upon reaction are ascorbic acid and sodium bicarbonate which react to form sodium ascorbate and carbon dioxide, as well as water. By way of example, ascorbic acid may be positioned in chamber 12 in the form of a liquid, such as by dissolving ascorbic acid in water. Sodium bicarbonate may be coated on, or otherwise positioned in, inner surfaces of the device, such as inner surfaces of the frame formed by the lumens 4, 6, 8. The chamber is sealed, such as by a membrane, to prevent leakage of the dissolved ascorbic acid. In use, the condom or construction ring is positioned over the penis. Manual pressure is applied to the chamber to break the membrane and release the ascorbic acid. Contact of the ascorbic acid with the sodium bicarbonate forms carbon dioxide that inflates the constriction ring or condom.

Another example of chemicals that produce carbon dioxide upon reaction are acetic acid and sodium bicarbonate. Products of the reaction of these materials are water, sodium ions, and acetate ions, which are not harmful to the user. Sodium bicarbonate may be provided in the form of baking soda. Acetic acid may be provided by vinegar, for example.

Other non-toxic gases may be used to inflate the frame construct. Another example of materials that produce carbon dioxide for inflation of the lumens forming the frame is citric acid and sodium bicarbonate. Citric acid is mixed with water to facilitate the reaction. Lemon juice is an example of a composition comprising citric acid and water and which can provide a liquid for the reaction. For example, 2 g of Citric Acid, 2.6 g of Sodium Bicarbonate and 20 ml of distilled water produced gas for inflation of the frame. The quantities of material to be used will depend on the particular materials used to produce the gas and the interior volume of the lumens to be filled with gas from reaction of the materials, and the degree of rigidity desired.

The reactive materials may be positioned in separate chambers 114, 116 formed within the first or proximal annular lumen 6, 106, 206. Alternatively, external chambers that communicate with the frame construct may be used. The chambers may be formed as separate compartments that communicate with the lumens or as chambers positioned in first annular lumen. The reactive materials are separated prior to mixing for reaction. Separation of the compartments or chambers may be provided by a membrane or membranes. The membrane(s) may be burst by manual pressure, such as by placing the first annular lumen between the thumb and forefinger and applying pressure to break the membrane, thereby releasing the reactive materials from their respective chambers. The reactive materials mix to initiate reaction and release of the gas into the plurality of lumens. The chamber for the materials may be otherwise positioned within the frame of lumens or externally to the frame (but communicating with the frame), since in preferred embodiments the lumens that comprise the frame communicate with each other.

In one embodiment, one of the agents is a liquid and another agent is a solid. When manual pressure is applied to the chamber 12 comprising the liquid, the manual pressure bursts a membrane 14 separating the reactive materials, releasing the liquid agent to mix with the solid agent. Gas produced by the reaction of the liquid agent and the solid agent achieves sufficient pressure and volume to escape the chambers through the lumens and inflate the frame and annular lumens.

The gas is produced in sufficient pressure and volume to inflate the condom. In an embodiment, the gas inflates an inflatable frame formed by the first annular lumen or ring 6, the second annular lumen or ring 8, and/or the plurality of interconnecting lumens 4. The gas pressure is sufficient to achieve the requirements of the invention of forming a condom that holds a partially erect penis 2 in position for sexual intercourse.

In an embodiment, the inflated first (proximal) annular lumen 6 is constructed, arranged and positioned in the condom so that first annular lumen applies constrictive pressure at the corpus *cavernosum* of the penis 2 when the condom is worn and inflated. Selection of a diameter of the first annular lumen that will provide the required pressure may be used in combination with construction of the first annular lumen from an elastic material. The inflated proximal annular lumen 6, 106, 206 applies pressure to the base of the penis to retain blood in the erection chambers (corpus *cavernosum*) of the penis. The inner diameter of the substantially gas impermeable ring shaped lumen is reduced, and the [The] inflated annular lumen acts as a venous constrictor. This property is preferred in some applications since the device is useful for men who have a form of erectile dysfunction, and mechanical assistance in maintaining blood within the penis during intercourse is desirable. The condom of this embodiment may also retard urination as the first annular lumen applies pressure to the penis.

In a preferred embodiment, the condom sheath 10 is positioned over the frame. The frame forms an internal skeletal structure for the condom 20 when the frame is inflated as described.

In another embodiment, the frame provides an exoskeletal structure relative to the sheath of the condom. In yet another embodiment, the frame is positioned between layers of a multiple layer sheath comprising an outer layer and an inner layer.

In one embodiment, the condom, according to the invention, is sufficiently flexible prior to inflation to allow the condom to be rolled similarly to the way prior art condoms are rolled for packaging. The condom is employed by unrolling the condom and fitting the condom on the penis 2, which may be partially erect. Manual pressure is applied to the chamber 12 at the appropriate point to burst the membrane or membranes 14, separating the materials and initiating chemical reaction. The reaction produces a gas to inflate the condom as described.

In another embodiment the agents are separated by the structure of the rolled and deflated condom. By way of example in one embodiment, the liquid agent is positioned at or near the base of the condom, such as in the first annular lumen 6. The solid agent is positioned at or near the tip, such as in the second annular lumen 8. The lumens 4 are pinched from rolling of the condom for packaging, thereby preventing mixing of the agents. Mixing occurs as the condom is unrolled, opening the lumens and allowing liquid to flow through the lumens and into the second annular ring to interact with the solid material.

In another embodiment a heat activated membrane separates the agents. The membrane is ruptured when exposed to body heat as the condom is worn and/or used, and for example, releases the liquid material from the chamber in which it is held. The agents mix as the membrane is ruptured.

Figure 8:
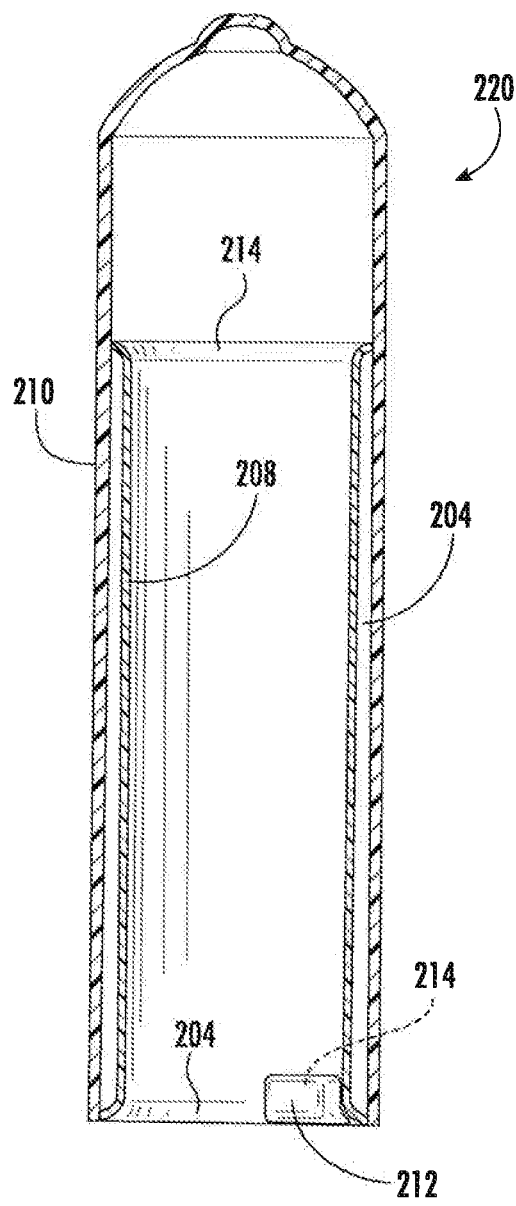
FIG. 8 is sectioned view of an embodiment of the condom showing an inflatable compartment formed between the sheath and a partial sheath of the condom.

In yet another embodiment, an inflation compartment lumen is formed between an outer sheath 210 of the condom a partial inner sheath 208. FIG. 8. The inflation compartment lumen (which is preferred to be an inflatable and substantially gas impermeable lumen) 204 communicates with and receives gas produced by the materials described herein, which inflates and elongates the condom for use. The inflation compartment lumen structure may be formed by a multiple layer structure comprising the partial inner sheath 208 and the outer sheath 210. The inflation compartment lumen may be formed by sealing 214, such as heat sealing the partial inner sheath to the outer sheath near the proximal end of the condom. The space between the substantially gas impermeable layers forms the inflation compartment lumen 204. The materials react to produce a gas for inflation of the inflation compartment formed between the layers. The partial sheath is referred to as "partial" because it preferably does not extend to the distal end of the condom, and in use, is positioned below the coronal sulcus so that only the outer sheath 210 covers the coronal sulcus.

An annular lumen 206 may be provided at the proximal end of condom that communicates with the inflation chamber lumen 204. A chamber 212 for a reactive material, such as a liquid material described herein, may be provided. A solid reactive material is also provided, which may be present in the chamber and separated from the liquid material prior to use. The solid material may be contained in the annular lumen or in the inflation compartment lumen.

In an example of use of the condom embodiments of the invention, the user's penis is inserted into a deflated condom constructed as described herein. The coronal sulcus should be positioned at or above the second or distal annular lumen 8 in the embodiment shown in FIG. 2 and at or above the partial inner sheath 208 for the embodiment shown in FIG. 8. The condom is preferred to be constructed so that the fully inserted penis will, in most applications, position the coronal sulcus at or just above the second annular lumen or partial inner sheath. After positioning the penis in the condom, the membrane associated with the chamber is broken to mix the reactive chemicals. The gas produced from reaction inflates the frame formed by the lumens, providing a construct that is sufficiently rigid for sexual intercourse.

Figure 5:
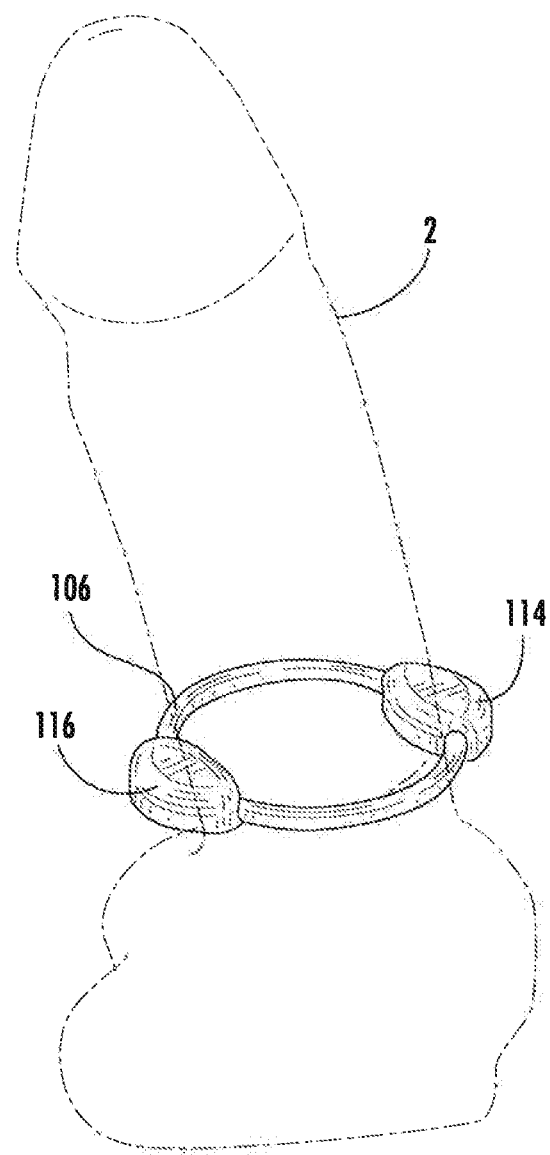
FIG. 5 shows an embodiment of a constriction ring positioned on a model of a penis.
Figure 6:
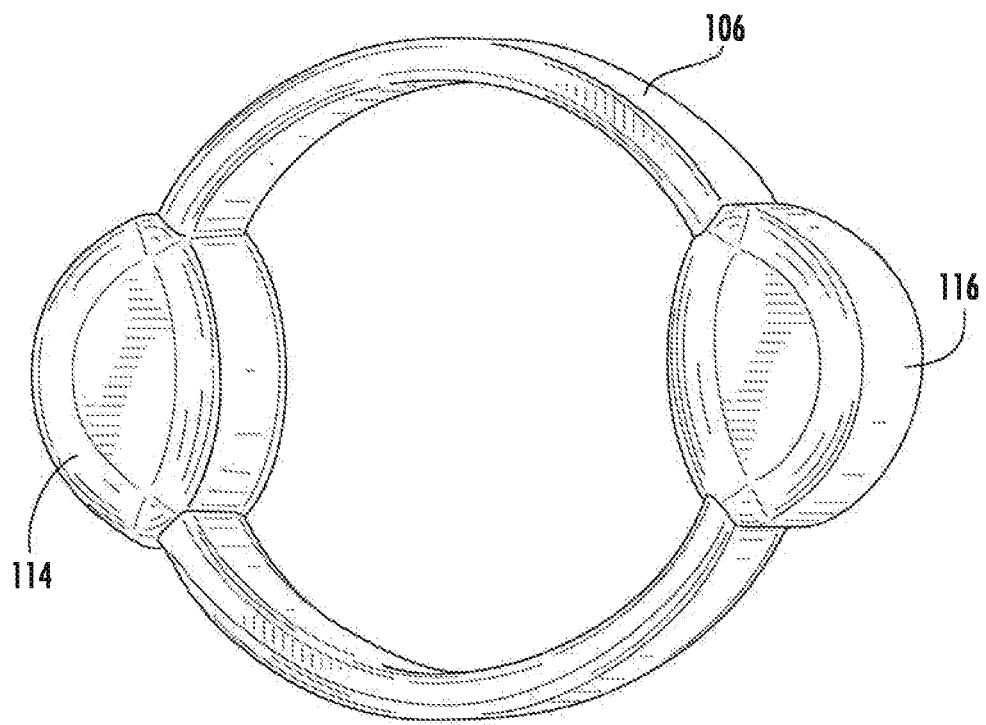
FIG. 6 shows a constriction ring prior to inflation.
Figure 7:
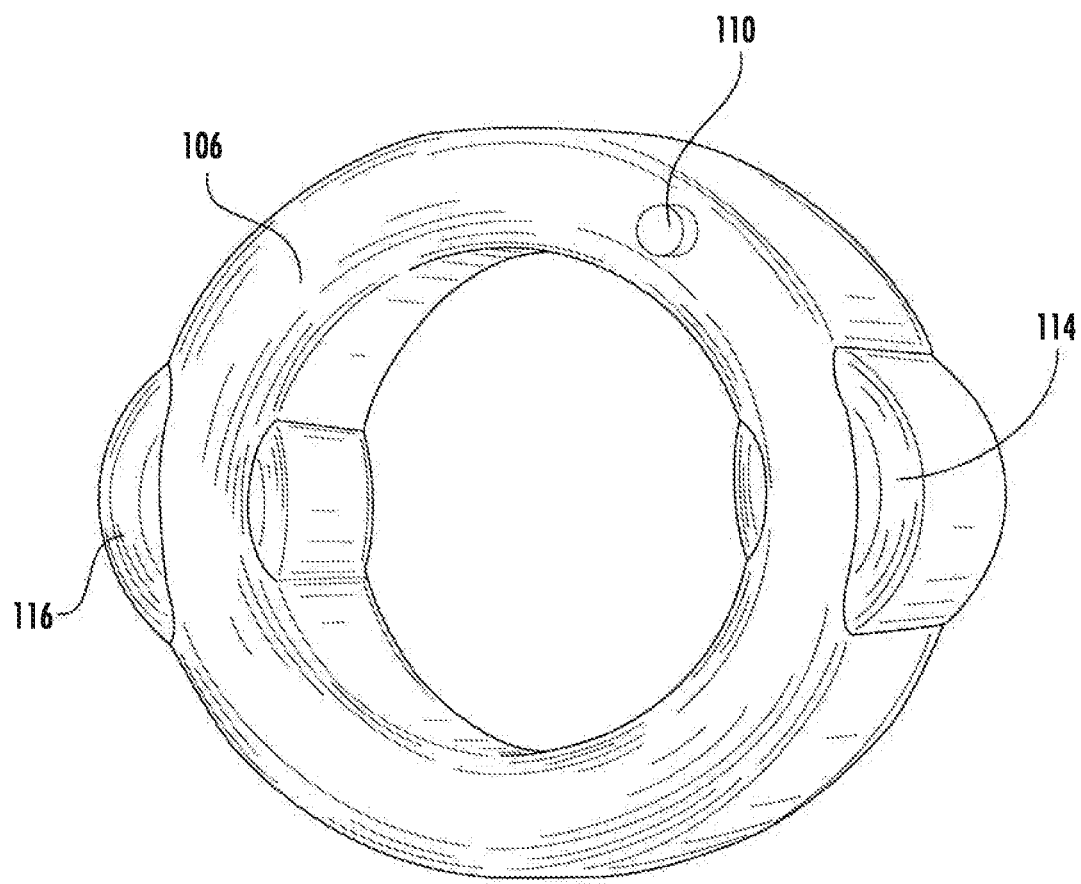
FIG. 7 shows an inflated constriction ring.

A constriction ring 106 may be constructed to self-inflate. FIGS. 5-7. As with an embodiment of the condom that comprises the inflated first (proximal) annular lumen 6, the annular constriction ring applies pressure to the base of the penis to retain blood in the erection chambers (corpus *cavernosum*) of the penis. A chamber or chambers 114, 116 may be provided to contain the reactive materials prior to mixing. The materials are provided as described herein for the full condom embodiments.

After use, the proximal annular lumen may be punctured for deflation, or the device is simply removed from the penis and discarded. In one embodiment a seal 110 is torn away from an annular lumen 6, 106, 206 or other part of the frame to release the inflation gas and deflate the condom or constriction ring.

As described above, the proximal annular lumen 6, 106, 206 may comprise chambers 14, 114, 116, 212 that are separated by a membrane, such as membrane 14, 214. The chambers hold one or more [the] reactive materials. Bursting the membrane mixes the reactive materials to supply gas from reaction. A chamber or chambers comprising reactive agents as described herein is provided for the constriction ring. Manual pressure is applied to the chamber at the appropriate point to burst a membrane or membranes to initiate a chemical reaction between materials separated by the membrane(s) and produce gas as described herein. The gas inflates the constriction ring to apply pressure to the base of the penis.

The constriction ring 106 in the embodiment shown does not comprise a condom or the frame of the condom according to the embodiments described for the condom. However, the constriction ring may be used with condoms known in the art or with a condom according to the invention by positioning the constriction ring over, or under, the condom sheath, or below, the condom and positioning the constriction ring at or near the base of the penis. FIG. 5. Also, annular lumen 6, 206 may be constructed as a constriction ring to constrict blood or urine flow from the penis when the device is in the form of a condom.

What is claimed is:

1. An inflatable sex aid, comprising an inflatable and substantially gas impermeable ring shaped lumen, a first material and a second material, wherein the first material reacts with the second material to produce a non-toxic gas, and the non-toxic gas inflates the inflatable and substantially gas impermeable ring shaped lumen.

2. An inflatable sex aid as described in claim 1, wherein the first material is a liquid.

3. An inflatable sex aid as described in claim 1, wherein the first material is a liquid and the second material is a solid.

4. An inflatable sex aid as described in claim 1, wherein the first material is a liquid contained within a chamber, and wherein the chamber is separated from the inflatable and substantially gas impermeable ring shaped lumen by a membrane.

5. An inflatable sex aid as described in claim 1, wherein the first material is a liquid contained within a chamber, and wherein the chamber is separated from the inflatable and substantially gas impermeable ring shaped lumen by a membrane, and wherein the inflatable and substantially gas impermeable ring shaped lumen comprises the second material.

6. An inflatable sex aid as described in claim 1, wherein the inflatable and substantially gas impermeable ring shaped lumen is annular.

7. An inflatable sex aid as described in claim 1, wherein the inflatable and substantially gas impermeable ring shaped lumen is annular, and an inner diameter of the inflatable and substantially gas impermeable ring shaped lumen is reduced upon inflation of the inflatable and substantially gas impermeable ring shaped lumen by the gas.

8. An inflatable sex aid as described in claim 1, wherein the first material is a liquid contained within a chamber, and wherein the chamber is separated from the inflatable and substantially gas impermeable ring shaped lumen by a membrane, and wherein the membrane is constructed and arranged to burst upon application of manual pressure.

9. An inflatable sex aid as described in claim 1, wherein the first material is a liquid contained within a chamber, and wherein the chamber is separated from the inflatable and substantially gas impermeable ring shaped lumen by a membrane, and wherein the membrane is constructed and arranged to burst upon exposure of the membrane to body heat.

10. An inflatable sex aid, comprising:
 a first material and a second material, wherein the first material reacts with the second material to produce a non-toxic gas,
 the inflatable sex aid further comprising a sheath and an inflatable frame, wherein the inflatable frame comprises an inflatable and substantially gas impermeable lumen and an inflatable and substantially gas impermeable elongated lumen, and the inflatable and substantially gas impermeable elongated lumen and the inflatable and substantially gas impermeable lumen receive the non-toxic gas, and the sheath is constructed and arranged to elongate as the inflatable frame formed by the inflatable and substantially gas impermeable elongated lumen and the inflatable and substantially gas impermeable lumen receives the non-toxic gas and the inflatable frame is inflated by the non-toxic gas.

11. An inflatable sex aid as described in claim 10, wherein the inflatable frame further comprises a second inflatable and substantially gas impermeable lumen, wherein the second inflatable and substantially gas impermeable lumen is positioned opposite the inflatable and substantially gas impermeable elongated lumen from the inflatable and substantially gas impermeable lumen, and the inflatable and substantially gas impermeable elongated lumen, the inflatable and substantially gas impermeable lumen, and the second inflatable and substantially gas impermeable lumen receive the non-toxic gas, and the sheath is constructed and arranged to elongate as the inflatable frame formed by the inflatable and substantially gas impermeable elongated lumen, the inflatable and substantially gas impermeable lumen and the second inflatable and substantially gas impermeable lumen receives the non-toxic gas and the inflatable frame is inflated by the non-toxic gas.

12. An inflatable sex aid as described in claim 10, wherein the sheath comprises an open end and a closed end, and wherein the inflatable frame does not extend to the closed end of the sheath.

13. An inflatable sex aid as described in claim 10, wherein the first material is a liquid contained within a chamber, and wherein the chamber is separated from the inflatable and substantially gas impermeable lumen by a membrane, and wherein the inflatable and substantially gas impermeable lumen comprises the second material.

14. An inflatable sex aid as described in claim 10, wherein the inflatable frame does not extend to a distal end of the sheath and a space is present between the inflatable frame and the sheath that is constructed and arranged to accept a distal end of a penis of user.

15. An inflatable sex aid as described in claim 10, wherein the inflatable and substantially gas impermeable lumen is annular, and an inner diameter of the inflatable and substantially gas impermeable lumen is reduced upon inflation of the inflatable and substantially gas impermeable lumen by the gas.

16. An inflatable sex aid as described in claim 10, wherein the first material is a liquid contained within a chamber, and wherein the chamber is separated from the inflatable and substantially gas impermeable lumen by a membrane, and wherein the membrane is constructed and arranged to burst upon exposure of the membrane to body heat.

17. An inflatable sex aid as described in claim 10, wherein the inflatable frame further comprises a second inflatable and substantially gas impermeable lumen, and a second inflatable and substantially gas impermeable elongated lumen, wherein the inflatable and substantially gas impermeable lumen is positioned near a proximal end of the inflatable frame, and the second inflatable and substantially gas impermeable lumen is positioned near a distal end of the inflatable frame, and the inflatable and substantially gas impermeable elongated lumen and the second inflatable and substantially gas impermeable elongated lumen connect the first inflatable and substantially gas impermeable lumen to the second inflatable and substantially gas impermeable lumen to form the inflatable frame, and the inflatable frame receives the non-toxic gas and is inflated by the non-toxic gas.

18. An inflatable sex aid, comprising:
an inflatable and substantially gas impermeable lumen,
a first material and a second material, wherein the first material reacts with the second material to produce a non-toxic gas, and the gas inflates the inflatable and substantially gas impermeable lumen,
wherein the inflatable sex aid is formed as a condom, the condom comprising a first sheath and a second sheath, wherein the inflatable and substantially gas impermeable lumen is formed between the first sheath and the second sheath.

19. An inflatable sex aid as described in claim 18, wherein a distal end of the second sheath does not extend to a distal end of the condom to form an enlarged and closed area of the condom at the distal end of the condom between the first sheath and the second sheath.

* * * * *